(12) United States Patent
Okura

(10) Patent No.: US 10,416,135 B2
(45) Date of Patent: Sep. 17, 2019

(54) PREPARATIVE LIQUID CHROMATOGRAPHIC APPARATUS

(71) Applicant: Yamazen Corporation, Osaka-shi, Osaka (JP)

(72) Inventor: Kihachiro Okura, Osaka (JP)

(73) Assignee: YAMAZEN CORPORATION, Osaka (JP)

( * ) Notice: Subject to any disclaimer, the term of this patent is extended or adjusted under 35 U.S.C. 154(b) by 0 days.

(21) Appl. No.: 15/403,543

(22) Filed: Jan. 11, 2017

(65) Prior Publication Data

US 2018/0196020 A1 Jul. 12, 2018

(51) Int. Cl.
*G01N 30/86* (2006.01)
*G01N 30/72* (2006.01)
*G01N 30/74* (2006.01)
*G01N 30/82* (2006.01)

(52) U.S. Cl.
CPC ......... *G01N 30/8651* (2013.01); *G01N 30/82* (2013.01)

(58) Field of Classification Search
CPC .... G01N 30/64; G01N 30/74; G01N 30/7233; G01N 30/8651; G01N 2030/027
See application file for complete search history.

(56) References Cited

U.S. PATENT DOCUMENTS

| | | | | |
|---|---|---|---|---|
| 2004/0132194 | A1* | 7/2004 | Bricker | B01J 19/0046 436/37 |
| 2014/0244185 | A1* | 8/2014 | Yamamura | H01J 49/0036 702/23 |
| 2015/0268203 | A1* | 9/2015 | Asano | G01N 30/72 250/288 |
| 2017/0067864 | A1* | 3/2017 | Kudo | H01J 49/0036 |
| 2017/0138916 | A1* | 5/2017 | Sumiyoshi | G01N 30/8696 |

FOREIGN PATENT DOCUMENTS

| | | |
|---|---|---|
| JP | H11 304783 A | 11/1999 |
| JP | 2004 325265 A | 11/2004 |
| JP | 2012 193999 | 10/2012 |

* cited by examiner

*Primary Examiner* — Christine A Enad
(74) *Attorney, Agent, or Firm* — Polsinelli PC

(57) ABSTRACT

A preparative liquid chromatographic apparatus comprising a column for separating components in a sample; a dispensing unit for dispensing an eluate from the column; a detector for the eluate; an analysis unit for the eluate; a display unit for displaying an analysis result a data storage unit; and an arithmetic control unit for controlling the display unit and the data storage unit. The analysis unit has at least one qualitative analysis unit for continuously and qualitatively analyzing the eluate. The display unit simultaneously displays a chromatogram acquired by the detector and the acquisition position of the dispensing unit and displays a correspondence relationship between each fraction and the chromatogram, and wherein by using the correspondence relationship between each fraction and the chromatogram shown in the display unit, the qualitative analysis data selected from the data storage unit is displayed on the display unit using the arithmetic control unit.

4 Claims, 2 Drawing Sheets

PREPARATIVE LIQUID CHROMATOGRAPHIC APPARATUS

CROSS REFERENCE TO RELATED APPLICATIONS

This application is based on Application No. 2014-0124407 filed in Japan on Jun. 17, 2017, which was published as JP 2016-003954 A on Jan. 12, 2016. The entire contents of this Japanese application are hereby incorporated by reference.

TECHNICAL FIELD

The present disclosure relates to a liquid chromatographic apparatus.

BACKGROUND OF THE INVENTION

The preparative liquid chromatographic apparatus is an apparatus for separating components in a solution in which a plurality of components are mixed according to the principle of chromatography using a difference in passing speed of different compounds through a column filler. In recent years, even in such preparative liquid chromatographs, the functions have been advanced and automated, and many attempts have been made to achieve efficient dispensing.

In such a preparative liquid chromatographic apparatus, the eluate after passing through a column is dispensed at regular time intervals. When such fraction separation is carried out, what kind of components are present in each dispensed fraction cannot be clarified without qualitative analysis.

For example, in the separation after performing a synthesis reaction, it is common to execute a qualitative analysis for the fraction after the dispensing in order to know which fraction includes the target compound, whether impurities are mixed in the fraction, or the like.

However, qualitative analysis needs sample adjustment such as concentration adjustment of dispensed fractions, which requires complicated labor.

Among chromatographic apparatuses for analysis such as HPLCs, an HPLC-MS with a mass spectrometer disposed downstream of the dispensing column is known. In general, however, such a device is a qualitative analysis unit for performing analysis, and installation of any other qualitative analysis unit in a preparative chromatographic apparatus has not been common.

The installation of a mass spectrometer in a preparative chromatographic apparatus is described in Patent Literature 1. However, according to Patent Literature 1, the mass spectrometer is installed not for the purpose of checking qualitative data of a fraction, but for the purpose of obtaining the timing of fractionation conducted by a fraction collector for acquiring a large amount of target sample, from the result of a mass spectrum. Therefore, the mass spectrometer is not intended to be used for obtaining the qualitative data of the fraction.

PRIOR TECHNICAL DOCUMENTS

Patent Documents

[Patent Document 1] Japanese Unexamined Patent Publication No. 2012-193999

SUMMARY OF INVENTION

Problems to be Solved by the Invention

An object of the present disclosure is to reduce labor for dispensing by a preparative liquid chromatographic apparatus by omitting labor for qualitative analysis after dispensing, by means of solution of the above-mentioned problem to ensure that qualitative analysis can be performed simultaneously with dispensing, the result of the obtained qualitative analysis can be easily called up, and the qualitative analysis result of the fraction can be calculated.

Means for Solving Object

The present disclosure relates to a preparative liquid column chromatographic apparatus provided with a column (A) for separating components in a sample, a dispensing unit (B) for dispensing an eluate from the column, a detector (C) for the eluate, an analysis unit (D) for the eluate, a display unit (E) for displaying an analysis result, a data storage unit (G) for storing data, and an arithmetic control unit (F) for controlling the display unit (E) and the data storage unit (G). In the preparative liquid chromatographic apparatus, the analysis unit (D) has at least one qualitative analysis unit for continuously and qualitatively analyzing the eluate, and the data storage unit (G) stores at least a measurement result of the detector (C), qualitative analysis data of an effluent analyzed by the analysis unit (D), and an acquisition position of each fraction dispensed by the dispensing unit (B). The display unit (E) simultaneously displays a chromatogram acquired by the detector (C) and the acquisition position of the dispensing unit (B) and displays a correspondence relationship between the each fraction and the chromatogram, and with respect to a specific dispensed sample designated in accordance with an observer's desire by using the correspondence relationship between the each fraction and the chromatogram shown in the display unit (E), the qualitative analysis data selected from the data storage unit (G) is displayed on the display unit (E) by using the arithmetic control unit (F).

The qualitative analysis unit utilizes preferably at least one selected from the group of ultraviolet absorption, mass spectrometry, and nuclear magnetic resonance (NMR).

The qualitative analysis data is preferably data obtained by integrating or averaging a plurality of measurement results in accordance with a designation by a measurer.

Effects of the Invention

According to the present disclosure, continuous qualitative data can be obtained in parallel with the execution of preparative liquid chromatography, and further such qualitative data can be easily associated with the separation and dispensing operation performed by the chromatograph. Hence, further qualitative analysis of each dispensed fraction is not needed, and the labor for separation operation in research and development can be greatly reduced.

DETAILED DESCRIPTION OF PREFERRED EMBODIMENTS

Figure 1:
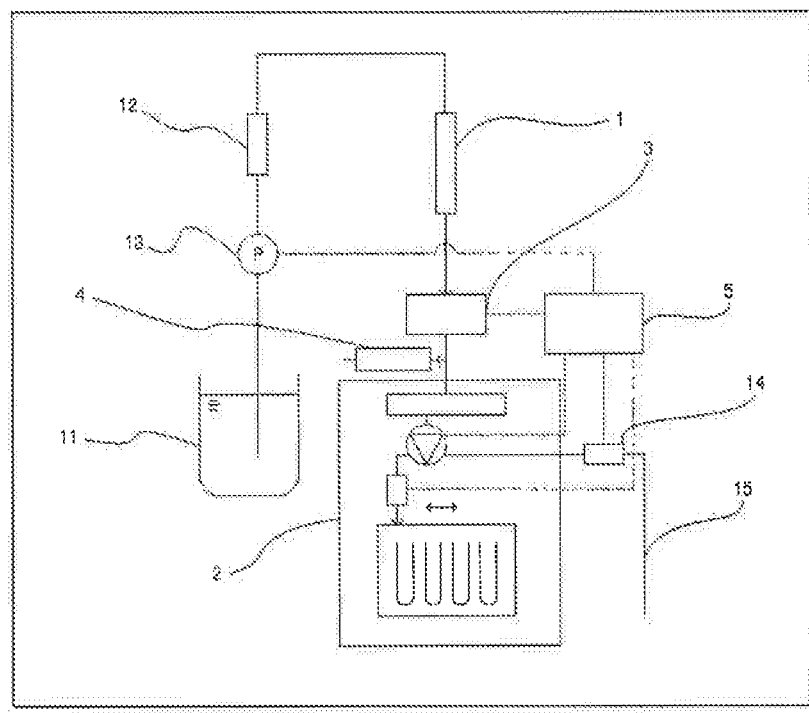
FIG. 1 is a schematic diagram showing an example of a configuration of a preparative liquid chromatographic apparatus of the present disclosure.

The preparative liquid chromatographic apparatus of the present disclosure is provided with a column (A) for separating components in a sample, a dispensing unit (B) for dispensing an eluate from the column, a detector (C) for the eluate, and an analysis unit (D) for the eluate.

Further, in order to control the preparative liquid chromatographic apparatus having the above-mentioned (A) to (D), the apparatus includes a display unit (E) for displaying an analysis result, an arithmetic control unit (F) for controlling the display unit, and a data storage unit (G) for storing data. These (E) to (G) can be a personal computer or the like storing a program capable of performing calculation, control, data storage, display, etc. to achieve the object described in detail below.

Among these, the column (A) for separating the components in the sample is not particularly limited, and any column to be used in preparative liquid chromatographic apparatus can be used.

The dispensing unit (B) for dispensing the eluate from the column described above is not particularly limited, and may be one dispensing manually or may be a fraction collector that dispenses fractions while automatically changing the fractions in accordance with a program.

The liquid chromatographic apparatus of the present disclosure has the detector (C). In the case of using the fraction collector as the above-mentioned dispensing unit (B), whether a dissolved component is present in the eluate is determined by the detector (C) to be described in detail below, and only the eluate containing the dissolved component is taken as a fraction and the eluate may be discarded when there is no dissolved component. A known system can be used as such a system.

The liquid chromatographic apparatus of the present disclosure has the detector (C). In other words, it is preferable to measure to determine whether a dissolved component is present in the eluate by the detector (C) and to carry out chromatography while confirming the elution position of the dissolved component. A detector commonly used for various chromatographic apparatuses can be used as the detector, and a method selected from the group of ultraviolet absorption, differential refractive index, evaporative light scattering, mass spectrometry, and circular dichroism can be used.

The function of the detector (C) may be carried out by the analysis unit (D) for the eluate which will be described in detail below, or the detector (C) may be provided separately from the analysis unit (D) for the eluate. Since the analysis unit (D) described in detail below is a unit for performing qualitative analysis, its analysis needs to clarify what type of compound the target compound is; however, the above-mentioned detector needs to confirm only the presence or absence of the eluted component, and thus, it is sufficient that analysis suitable for such a purpose is carried out by the detector.

The measurement result made by the above-mentioned detector (C) is also sent to and stored in the data storage unit (G).

According to the present disclosure, the eluate having passed through the column (A) is dispensed by the dispensing unit (B) and is obtained as a single fraction or a plurality of fractions such as fractions 1, 2 and 3. As described above, fractions are acquired automatically or manually, but in either case, each fraction is associated with information on the acquisition such as the flow-out time or the flow-out amount when the fraction is acquired, and the data is stored in the data storage unit (G).

Fraction data is made by associating a fraction with the acquired flow-out time such that fraction 1 is a fraction obtained during the period from 0 to 10 seconds after the flow-out start and fraction 2 is a fraction obtained during the period from 1 to 2 minutes after the flow-out start for example, or alternatively by associating a fraction with the flow-out amount such that fraction 1 is a fraction associated with the flow-out amount of from 0 to 5 ml after the flow-out start and fraction 2 is a fraction associated with the flow-out amount of from 5 to 10 ml after the flow-out start for example, and the data is stored in the data storage unit (G).

The preparative liquid chromatographic apparatus of the present disclosure is operated while displaying the detection result of the above-mentioned detector (C) and the fraction data of the dispensing unit (B) superposed on each other on the display unit (E). Such a display state on the screen is shown in FIG. 2.

Figure 2:
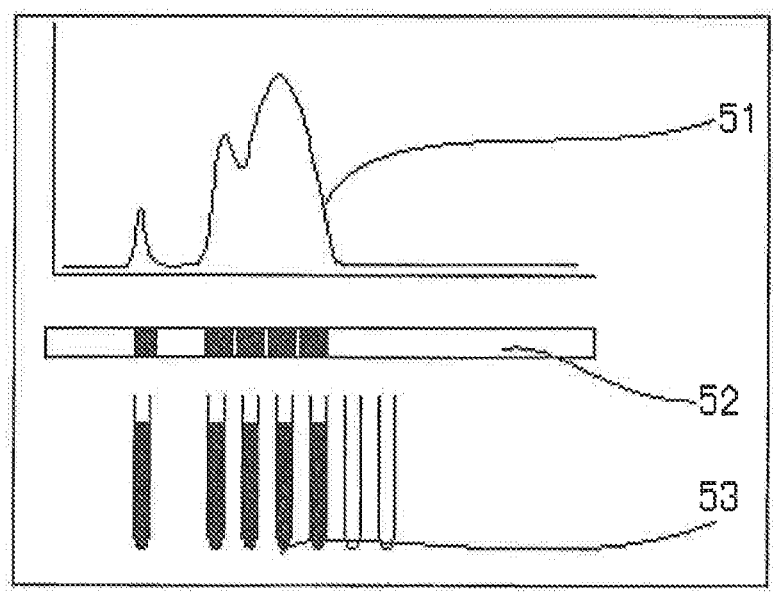
FIG. 2 is a diagram showing an example of display on the image display device of the preparative liquid chromatographic apparatus of the present disclosure.

FIG. 2 shows a state where the measurement result 51 by the detector (C) and the fraction data 52 and 53 are displayed on the screen.

In FIG. 2, the horizontal axis indicates time or the flow-out amount, and the vertical axis indicates the detection result of the detector. Further, fraction data by the dispensing unit (B) is displayed corresponding to the common horizontal axis (that is, acquisition positions of fractions). By referring to such a screen, which peak of the detector (C) each fraction corresponds to can be instantaneously determined. For this reason, the compound in the fraction can be accurately analyzed when the result of the analysis carried out later by the analysis unit (D) is associated with the fraction.

Further, the fraction data 52 shows what time each fraction was acquired or how much flow-out amount of each fraction was acquired. From FIG. 2 like this, which flow-out peak each fraction corresponds to can be determined during the measurement. The fraction data 53 shows the number of fractions obtained so far and the obtained solution amount of each fraction.

The preparative liquid chromatographic apparatus of the present disclosure has at least one qualitative analysis unit for continuously and qualitatively analyzing the eluate as the analysis unit (D). That is, qualitative analysis of the effluent is continuously performed, and the obtained data is stored in the data storage unit (G).

The above-mentioned analysis unit (D) is not particularly limited as long as it is an analysis unit capable of qualitatively analyzing a compound to be separated and confirming the separation of the target compound, and examples using methods of ultraviolet absorption, mass spectrometry, and nuclear magnetic resonance (NMR) can be cited for example. The unit may be provided with two or more of these functions. The qualitative analysis needs to be conducted to the extent so that it can be confirmed that the object is the target object and that the object is separated with the degree of purity desired by the observer.

For example, in the case of ultraviolet absorption, what is measured is not the absorbance of a single wavelength but the ultraviolet absorption at wavelengths in a wide range. By this configuration, whether the target compound exists in high concentration in a predetermined fraction can be easily determined by confirming the absorption pattern.

Further, for a mass spectrum, it is necessary to prepare a chart in which the measured molecular weight is recorded. As a result, similarly to the ultraviolet absorption described above, the target substance can be identified and the presence of impurities can also be confirmed.

Furthermore, in recent years, the NMR analysis methods have been improved, and attempts have been made to link an NMR function to a chromatograph as a detection unit for various chromatographs. These known methods may be applied to the present disclosure and the NMR measurement of the eluate after separation may be continuously performed.

In the case of an analysis which does not cause decomposition by the analysis such as ultraviolet absorption analysis, the analysis unit (D) is installed on the flow-out line, and the effluent after the analysis is directly guided into the fraction, and in the case of the analytical method in which the sample is decomposed by the analysis such as mass spectrometry or the like, a part of the effluent may be introduced into a measurement line to be continuously measured.

Each of these analyzers constituting the analysis unit (D) is commercially available, and the whole integrated apparatus can be used by combining the unit with a preparative liquid chromatographic apparatus and by providing a computer that stores a control program.

Since the preparative liquid chromatographic apparatus of the present disclosure has the above-described configuration, on the screen display as shown in FIG. 2, the observer designates the position where the required qualitative analysis data is obtained by the analysis unit (D) while referring to the data of the detector (C) and the fraction data. In this manner, the qualitative analysis data designated by the observer is displayed on the display unit (E).

By such position designation by the observer, desired qualitative analysis data can be easily obtained, and analysis data at the time of dispensing by the preparative liquid chromatographic apparatus can be acquired extremely efficiently and accurately.

Designation of the acquisition position of the qualitative analysis data by the observer may be done by a measurement result at a specific point or may be done by a value of integral or an average value of measurement result within a specific range. The value of integral or the average value is preferably adopted because it reflects the whole composition within the specified range. Adopting a value of integral or an average value allows the measurement data to correspond to the composition of a specific fraction for example and thus is further preferable.

The instruction by the observer is not particularly limited. When a specific point of the measurement result by the detector is designated for example, the analysis result by the analysis unit (D) at this time can be displayed on the screen.

Figure 3:
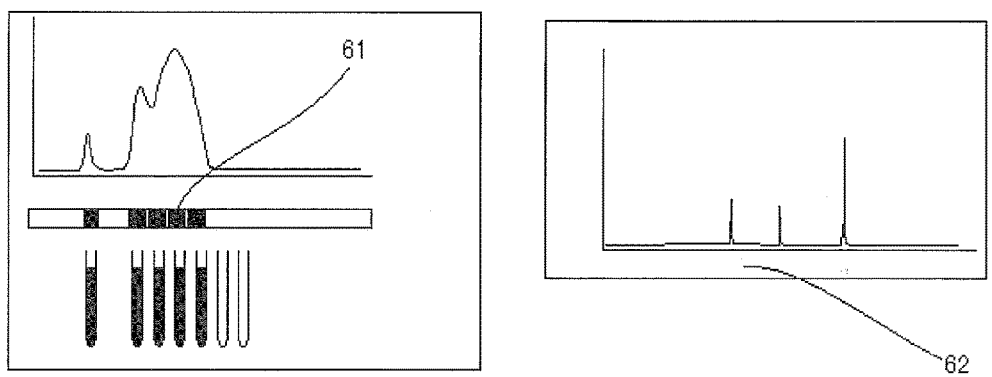
FIG. 3 is a diagram showing a state in which qualitative analysis data is displayed in an example of display on the image display device of the preparative liquid chromatographic apparatus of the present disclosure.

Further, as shown in FIG. 3, when the specific fraction 61 indicated in the fraction information is designated, the analysis result 62 corresponding to the fraction 61 is displayed on the screen. In this case, the data to be displayed may be a representative measurement value in the fraction, or may be the value of integral or the average value of the measurement result within the acquisition time corresponding to the acquisition time of the fraction based on the fraction information.

Figure 4:
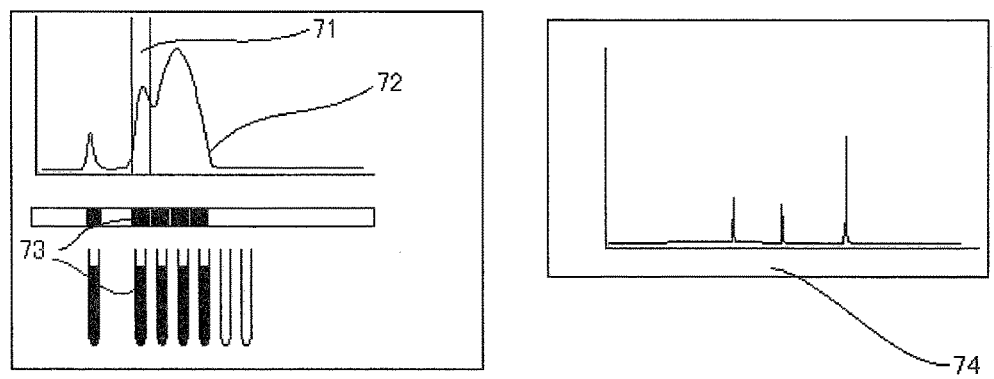
FIG. 4 is a diagram showing a state in which qualitative analysis data is displayed in an example of display on the image display device of the preparative liquid chromatographic apparatus of the present disclosure.

Further, as shown in FIG. 4, the observer designates the observation range 71 on the basis of the chromatogram, and the value of integral or the average value of the analysis result by the analysis unit (D) within the range may be displayed as the qualitative analysis result 74. In addition, when the observation is carried out by using such a method, it can be easily known that the corresponding fraction is the fraction 73.

In this way, by viewing the qualitative analysis result displayed in the diagrams on the right side of FIGS. 3 and 4, the observer can know whether the target substance has been acquired, or whether impurities exist, and qualitative analysis work for confirmation is not necessary. Furthermore, when unexpected peaks are present, qualitative data can be obtained to determine what kind of compound the unexpected peak is derived from.

An example of the preparative liquid chromatographic apparatus of the present disclosure is shown in FIG. 1 as a schematic view. It should be noted that the present disclosure is not limited to the example shown in FIG. 1. In FIG. 1, the presence or absence of a dissolved component in the effluent flowing out from the column 1 is confirmed by the detector 3, and the measurement result is stored in the data storage unit (G) for storing data, and is displayed on the display unit (E) simultaneously with the measurement.

A part of the effluent having left the detector is sent to the qualitative analysis unit 4 and qualitative analysis is carried out. The result is stored in the data storage unit (G).

In the example of FIG. 1, the effluent from the detector 3 is sent to the fraction collector 2, and only the necessary part is acquired as a fraction with reference to the measurement result of the detector 3, and the unnecessary part is discharged through a drain pipe 15. The fraction data in the fraction collector 2 is stored in the data storage unit (G) and displayed on the display unit (E) simultaneously with the measurement.

With regard to the data obtained in this way and stored in the data storage unit (G), by allowing the display unit (E) to display the data stored in the storage unit (G) using the arithmetic control unit (F) as necessary, the above-described object of the present disclosure can be achieved.

INDUSTRIAL APPLICABILITY

With the preparative liquid chromatographic apparatus of the present disclosure, qualitative analysis of the fraction can be performed simultaneously with dispensing. This makes it unnecessary to perform further qualitative analysis of fractions after dispensing in research and development, it is possible to omit work in separation and to conduct research and development more efficiently.

EXPLANATION OF REFERENCES

1 column
2 fraction collector
3 detector
4 qualitative analysis unit
5 controller
11 eluate
12 injector
13 pump
14 liquid sensor
15 drain pipe 51, 72 chromatogram
52, 53 fraction data
61 selected fraction
62, 74 qualitative analysis data displayed on the display unit
71 acquisition range of qualitative analysis data selected from the chromatogram
73 fraction corresponding to the qualitative analysis data acquisition range

The invention claimed is:

1. A preparative liquid chromatographic apparatus comprising:
   a column (A) for separating components in a sample;
   a dispensing unit (B) for dispensing an eluate from the column, wherein the dispensing unit (B) is a fraction collector;
   a detector (C) for the eluate;
   an analysis unit (D) for the eluate;
   a measurement line into which a part of the effluent is introduced to be continuously measured;
   a display unit (E) for displaying an analysis result;
   a data storage unit (G) for storing data; and
   an arithmetic control unit (F) for controlling the display unit (E) and the data storage unit (G),
   wherein the analysis unit (D) has at least one qualitative analysis unit for continuously and qualitatively analyzing the eluate, and the data storage unit (G) stores at least a measurement result of the detector (C), qualitative analysis data of an effluent analyzed by the analysis unit (D), and an acquisition position of each fraction dispensed by the dispensing unit (B),
   wherein the display unit (E) simultaneously displays a chromatogram acquired by the detector (C) and the acquisition position of the dispensing unit (B) and displays a correspondence relationship between the each fraction and the chromatogram, and
   wherein with respect to a specific dispensed sample designated in accordance with an observer's desire by using the correspondence relationship between the each fraction and the chromatogram shown in the display unit (E), the qualitative analysis data obtained by integrating or averaging a plurality of measurement results of the fraction selected from the data storage unit (G) is displayed on the display unit (E) by using the arithmetic control unit (F).

2. The preparative liquid chromatographic apparatus according to claim 1, wherein the qualitative analysis unit utilizes at least one selected from a group of ultraviolet absorption, mass spectrometry and NMR.

3. The preparative liquid chromatographic apparatus according to claim 2, wherein the qualitative analysis data is obtained by integrating or averaging the data corresponding to a flow-out time of the fraction or corresponding to a flow-out amount of the fraction.

4. The preparative liquid chromatographic apparatus according to claim 1, wherein the qualitative analysis data is obtained by integrating or averaging the data corresponding to a flow-out time of the fraction or corresponding to a flow-out amount of the fraction.

* * * * *